United States Patent [19]

Kieturakis

[11] Patent Number: 5,653,726
[45] Date of Patent: Aug. 5, 1997

[54] RETROGRADE DISSECTOR AND METHOD FOR FACILITATING A TRAM FLAP

[75] Inventor: Maciej J. Kieturakis, San Carlos, Calif.

[73] Assignee: Archimedes Surgical, Inc., Menlo Park, Calif.

[21] Appl. No.: 645,321

[22] Filed: May 13, 1996

Related U.S. Application Data

[63] Continuation of Ser. No. 334,656, Nov. 3, 1994, abandoned.

[51] Int. Cl.[6] .................................................. A61B 17/00
[52] U.S. Cl. ........................... 606/190; 128/898; 606/192
[58] Field of Search ........................ 606/190, 192, 606/1, 159, 170, 201, 204; 604/902; 128/898, 304–305, 305.1, 310, 341, 357, 20; 433/141

[56] References Cited

U.S. PATENT DOCUMENTS

| | | | |
|---|---|---|---|
| 936,379 | 10/1909 | Stevens. | |
| 1,213,005 | 1/1917 | Pillsbury. | |
| 3,096,962 | 7/1963 | Meijs. | |
| 3,545,443 | 12/1970 | Ansari | 128/347 |
| 3,730,185 | 5/1973 | Cook et al. | 606/190 X |
| 4,191,191 | 3/1980 | Auburn | 128/347 |
| 4,217,889 | 8/1980 | Radovan et al. | 128/1 R |
| 4,243,050 | 1/1981 | Littleford | 128/784 |
| 4,312,353 | 1/1982 | Shahbabian | 128/344 |
| 4,345,606 | 8/1982 | Littleford | 128/784 |
| 4,357,940 | 11/1982 | Muller | 606/190 X |
| 4,411,654 | 10/1983 | Boarini et al. | 604/165 |
| 4,535,773 | 8/1985 | Yoon | 604/51 |
| 4,574,806 | 3/1986 | McCarthy | 128/334 R |
| 4,581,025 | 4/1986 | Timmermans | 604/264 |
| 4,601,710 | 7/1986 | Moll | 604/165 |
| 4,644,936 | 2/1987 | Schiff | 128/1 D |
| 4,654,030 | 3/1987 | Moll et al. | 604/165 |
| 4,709,679 | 12/1987 | Muller | 606/190 X |
| 4,738,666 | 4/1988 | Fuqua | 604/280 |
| 4,769,038 | 9/1988 | Bendavid et al. | 623/13 |
| 4,772,266 | 9/1988 | Groshong | 604/164 |
| 4,793,348 | 12/1988 | Palmaz | 128/325 |
| 4,802,479 | 2/1989 | Haber et al. | 128/344 |
| 4,836,205 | 6/1989 | Barrett | 128/340 |
| 4,854,316 | 8/1989 | Davis | 128/334 R |
| 4,867,404 | 9/1989 | Harrington et al. | 248/231.4 |
| 4,881,537 | 11/1989 | Henning | 604/84 |
| 4,888,000 | 12/1989 | McQuilkin et al. | 604/164 |
| 4,931,042 | 6/1990 | Holmes et al. | 604/164 |
| 4,955,895 | 9/1990 | Sugiyama et al. | 606/194 |
| 4,959,067 | 9/1990 | Muller | 606/190 |

(List continued on next page.)

FOREIGN PATENT DOCUMENTS

| 512456 | 9/1939 | European Pat. Off. . |
| 2157727 | 8/1973 | Germany . |

OTHER PUBLICATIONS

George Ferzli et al., "Extraperitoneal Endoscopic Pelvic Lymph Node Dissection", J. Laparoendoscopic Surgery, vol. 1 (1992), pp. 39–44.

*Primary Examiner*—Guy V. Tucker
*Assistant Examiner*—Nancy Connolly Mulcare
*Attorney, Agent, or Firm*—Skjerven, Morrill, MacPherson, Franklin & Friel; Norman R. Klivans

[57] ABSTRACT

For surgery, an endoscopic retrograde dissector instrument and less invasive method for bluntly dissecting tissue planes overlying and underlying a rectus abdominus muscle to mobilize the muscle in a transverse abdominal mastoplasty (breast reconstruction). The retrograde dissector includes an elongate blunt-tipped guide member that carries a distal inflatable sleeve. The blunt tip of the guide member is advanced distally along a plane in the interior of the body thereby creating a small diameter dissected track. The distal inflatable sleeve is inflated and then pulled in a retrograde movement along the track to dissect a wide tissue plane laterally on each side of the track in a single efficient step. A pulse mechanism rapidly pulsates the inflated sleeve to facilitate the dissection of connective tissues along planes of least resistance to create a relatively blood-free dissected tissue plane.

13 Claims, 8 Drawing Sheets

U.S. PATENT DOCUMENTS

| | | | |
|---|---|---|---|
| 5,022,414 | 6/1991 | Muller | 606/190 |
| 5,030,206 | 7/1991 | Lander | 604/164 |
| 5,030,227 | 7/1991 | Rosenbluth et al. | 606/192 |
| 5,074,871 | 12/1991 | Groshong | 606/170 |
| 5,104,383 | 4/1992 | Shichman | 604/167 |
| 5,116,318 | 5/1992 | Hillstead | 604/96 |
| 5,116,353 | 5/1992 | Green | 606/184 |
| 5,116,357 | 5/1992 | Eberbach | 606/213 |
| 5,122,155 | 6/1992 | Eberbach | 606/213 |
| 5,127,917 | 7/1992 | Niederhauser et al. | 606/191 |
| 5,137,512 | 8/1992 | Burns et al. | 604/96 |
| 5,147,302 | 9/1992 | Euteneuer et al. | 604/103 |
| 5,147,316 | 9/1992 | Castillenti | 604/164 |
| 5,147,374 | 9/1992 | Fernandez | 606/151 |
| 5,147,376 | 9/1992 | Pianetti | 606/170 |
| 5,158,545 | 10/1992 | Trudell et al. | 604/53 |
| 5,176,692 | 1/1993 | Wilk et al. | 606/151 |
| 5,188,630 | 2/1993 | Christoudias | 606/1 |
| 5,195,507 | 3/1993 | Bilweis | 128/20 |
| 5,201,325 | 4/1993 | McEwen et al. | 428/779 |
| 5,201,742 | 4/1993 | Hasson | 606/130 |
| 5,203,773 | 4/1993 | Green | 606/104 |
| 5,209,736 | 5/1993 | Stephens | 604/164 |
| 5,222,970 | 6/1993 | Reeves | 606/195 |
| 5,224,952 | 7/1993 | Deniega et al. | 606/184 |
| 5,226,890 | 7/1993 | Ianniruberto et al. | 604/164 |
| 5,232,446 | 8/1993 | Arney | 604/96 |
| 5,232,451 | 8/1993 | Freitas et al. | 606/174 |
| 5,258,003 | 11/1993 | Ciaglia et al. | 606/185 |
| 5,269,753 | 12/1993 | Wilk | 604/49 |
| 5,271,380 | 12/1993 | Riek et al. | 128/4 |
| 5,279,567 | 1/1994 | Ciaglia et al. | 604/117 |
| 5,284,130 | 2/1994 | Ratliff | 128/20 |
| 5,308,327 | 5/1994 | Heaven et al. | 604/96 |
| 5,312,357 | 5/1994 | Buijs et al. | 6094/164 |
| 5,334,185 | 8/1994 | Giesy et al. | 604/164 |
| 5,336,237 | 8/1994 | Chin et al. | 606/167 |
| 5,346,504 | 9/1994 | Ortiz et al. | 606/192 |
| 5,348,541 | 9/1994 | Lyell | 604/164 |
| 5,352,234 | 10/1994 | Scott | 606/170 |
| 5,358,507 | 10/1994 | Daily | 606/159 |
| 5,368,598 | 11/1994 | Hasson | 606/119 |
| 5,370,109 | 12/1994 | Cuny | 128/20 |

RETROGRADE DISSECTOR AND METHOD FOR FACILITATING A TRAM FLAP

This application is a continuation of application Ser. No. 08/334,656, filed Nov. 3, 1994, now abandoned.

CROSS-REFERENCE TO RELATED APPLICATIONS

This application is related to co-pending and commonly invented U.S. patent applications Ser. No. 08/525,273, filed Jun. 1, 1994 now U.S. Pat. No. 5,569,183 issued Oct. 29, 1996, and Ser No. 08/316,164 filed Sept. 30, 1994.

BACKGROUND OF THE INVENTION

1. Field of the Invention

This invention relates to surgical instrumentation and more particularly to an instrument and method for dissecting connective tissues along a plane between muscle layers to mobilize a muscle in reconstruction of a breast after a mastectomy or for other plastic surgery.

2. Description of the Prior Art

Following a mastectomy, a breast may be reconstructed in certain patients with importation of a vascularized flap. The two most frequently employed options of importing such flaps are a latissimus dorci mycutaneous flap procedure and a transverse abdominal mastoplasty (TRAM flap). In such procedures, varying amounts of skin are transferred from either the patient's back or abdomen to a breast in a single operative procedure, along with intact muscle and an intact arteriovenous system. In current practice, muscles are mobilized in such flap procedures in an open surgical approach by dissecting around the muscle and arteriovenous system with conventional sharp dissecting instruments which is time-consuming.

SUMMARY OF THE INVENTION

An instrument in accordance with the present invention is adapted for dissecting connective tissues in planes around a muscle and is described with reference to the exemplary method of facilitating a TRAM flap procedure. The principal advantage of the TRAM flap procedure for breast reconstruction is the fact that the breast contour is created entirely by the importation of autogenous tissue without the need for an implantable prosthesis.

In general, the TRAM Flap "retrograde dissector" instrument in accordance with the invention is utilized to mobilize the contralateral rectus abdominus muscle along with the superior epigastric artery. The instrument includes an elongate 10 mm. diameter blunt-tipped guide member that is used to bluntly dissect a pathway along planes underlying and overlying the rectus abdominus muscle from a lower abdominal incision to an upper abdominal location. The instrument includes an optic lumen affording the surgeon contemporaneous endoscopic vision through the transparent distal tip of the guide as it is pushed along a plane between muscle layers. Optic fibers transmit light through the distal tip of the guide to illuminate the plane being dissected.

The distal portion of the retrograde dissector carries an inflatable elastomeric sleeve that assumes a delta-type plan shape upon expansion with an elliptical transverse sectional shape. The guide member further includes a "pulse" mechanism for pulsing the inflation medium within the inflation sleeve in any contracted or expanded position. Pulsation of the sleeve facilitates the blunt dissection of strong connective tissues that adhere between muscle layers. An insufflation channel is provided to simultaneous insufflate the dissected plane in front of the instrument's tip to enhance endoscopic vision. The instrument is made typically of plastic, including inexpensive plastic optics, and may be disposable or reusable.

In performing the method in accordance with the present invention, the surgeon makes a small incision in the patients lower abdomen overlying the rectus abdominus muscle. The surgeon then identifies the plane overlying the muscle or the anterior rectus sheath and advances the tip of the guide upward along the plane to a location near the costal margin (lower rib area). The surgeon thus bluntly dissects a small-diameter track or pathway while contemporaneously viewing (on a video monitor) the plane being dissected in front of the guide tip. The surgeon may simultaneously insufflate the plane to better view anatomic structures along the plane.

The surgeon then inflates the distal elastomeric sleeve which expands to a flattened transverse sectional shape with laterally-extending side portions that are adapted to dissect outwardly along the plane. The surgeon then pulls (proximally) the retrograde dissector back through the small-diameter dissected track causing the delta-shaped sleeve to bluntly dissect connective tissues laterally outward from the track along planes of least resistance. The surgeon pulses the inflatable sleeve during the retrograde movement of the sleeve to facilitate the dissection.

The surgeon may withdraw the expanded sleeve in one step through the skin incision because the elastic sleeve will progressively deform through "hour-glass" shapes as it exits the incision, without substantially tearing the skin layer. The surgeon then identifies the plane underlying the rectus abdominus muscle and again advances the guides tip upwardly toward the costal margin. The inflatable sleeve again is expanded and then withdrawn along the dissected track to dissect the plane underlying the muscle rectus abdominus thereby mobilizing the muscle. Thereafter, the lower end of the muscle is transsected and the abdominal skin flap attached to the muscle is imported to the breast through the dissected plane. Thus, in rapid steps of advancing the retrograde dissector, then withdrawing the inflated sleeve along the dissected track, the surgeon may dissect connective tissues along planes both above and below the abdominal rectus muscle through a single minimally invasive incision.

The present TRAM flap dissector is to be contrasted with the disclosure of U.S. Pat. No. 5,569,183 referenced above. U.S. Pat. No. 5,569,183 discloses an elongate guide with a transparent inflatable envelope that is expanded in a fixed location to bluntly dissect a viewing space in the interior of the body. U.S. Pat. No. 5,569,183 also discloses a method for endoscopically viewing a surgical procedure performed around the surface of the transparent expanded envelope.

The present invention also is to be contrasted with U.S. Pat. No. 5,496,345 issued Mar. 5, 1996 to Kieturakis, Mollenaur and Monfort which discloses a large volume low-pressure non-elastomeric balloon that is carried into the interior of the body and inflated in a fixed position. The large balloon of U.S. Pat. No. 5,496,345 issued Mar. 5, 1996 to Kieturakis, Mollenaur and Monfort is suitable for dissecting the peritoneum (a thin membrane) away from the abdominal wall to create an insufflated space. U.S. Pat. No. 5,496,345 issued Mar. 5, 1996 to Kieturakis, Mollenauar and Monfort also discloses a method of performing a surgical procedure, i.e., a hernia repair, in the insufflated properitoneal space.

In general, the present retrograde dissector provides an elongate guide member and method for bluntly dissecting a small diameter track through connective tissues along a plane in the interior of the body between a first and second location. The present instrument and method allow contemporaneous vision through the guide member as it traverses from the first location to the second location.

The present instrument and method provide an inflated structure which is withdrawn in reverse through a dissected track to bluntly dissect connective tissues along lines of least resistance thereby creating a relatively bloodless dissected plane. Also an inflatable structure expands to assume a flattened elliptical transverse sectional shape for dissecting laterally outward along a plane. An inflation medium is pulsed within an inflatable structure to facilitate tissue dissection during the retrograde movement of the inflatable structure along a plane.

A method in accordance with the invention for withdrawing an inflated structure in a single retrograde motion thus bluntly dissects connective tissues along a plane between a first location to a second remote location in a simple efficient manner.

An inflation medium is pulsed or resonated within an inflatable structure with an ultrasonic transducer that produces frequencies ranging from 5 kHz to 100 kHz to transfer mechanical motion to tissue surrounding an expanded inflatable sleeve to denature protein within tissues and to heat tissues by internal tissue friction thereby cauterizing dissected blood vessels.

An instrument in accordance with the present invention is inexpensive and may be disposable. Additional advantages and features of the present invention will appear in the following description.

DETAILED DESCRIPTION OF THE PRESENT INVENTION

By way of example, FIGS. 1–4 illustrate retrograde dissector 5 that is adapted for a TRAM flap procedure. Retrograde dissector 5 has elongate plastic guide sleeve 10 with proximal and distal ends, 11 and 12. Guide sleeve 10 with central bore 14 is made of metal or plastic and is preferably transparent medical grade plastic. The overall length of guide sleeve 10 along axis 15 for a TRAM flap procedure is approximately 350 mm. (not limiting). The outer diameter of guide sleeve 10 is approximately 10 mm. (not limiting). Distal end 12 of sleeve 10 has a rounded or blunt transparent tip 17 enclosing bore 14. The distal portion 19 of sleeve 10 has a reduced diameter to accommodate the thickness of the wall of inflatable elastomeric sleeve member 20 described further below. Inflatable sleeve 20 in the contracted position contracts to the outer diameter of guide sleeve 10.

Figure 1:
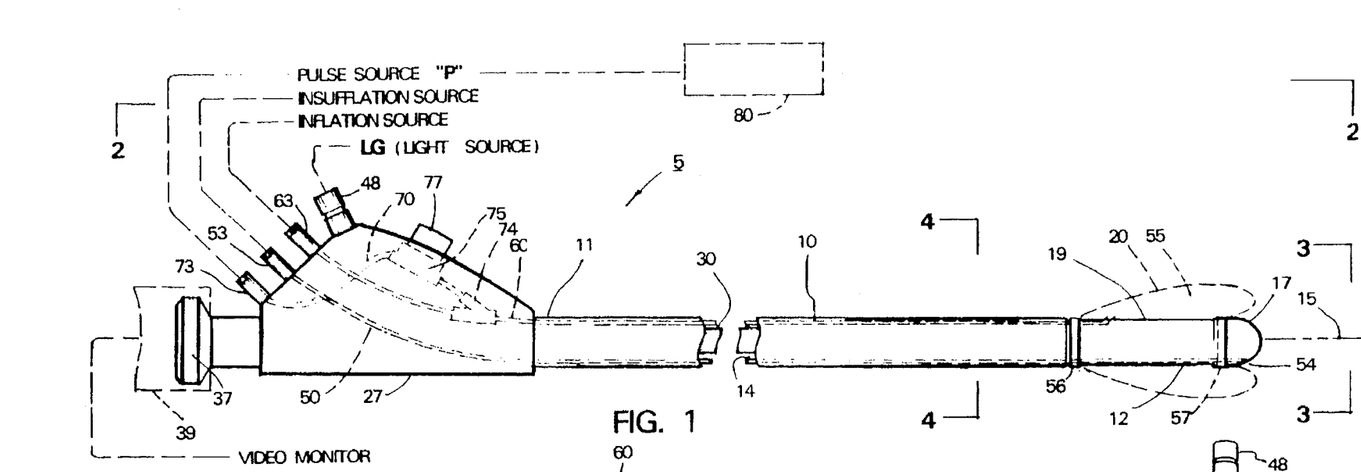
FIG. 1 is a side elevational view of an embodiment of the present invention.
Figures 2, 3, 4:
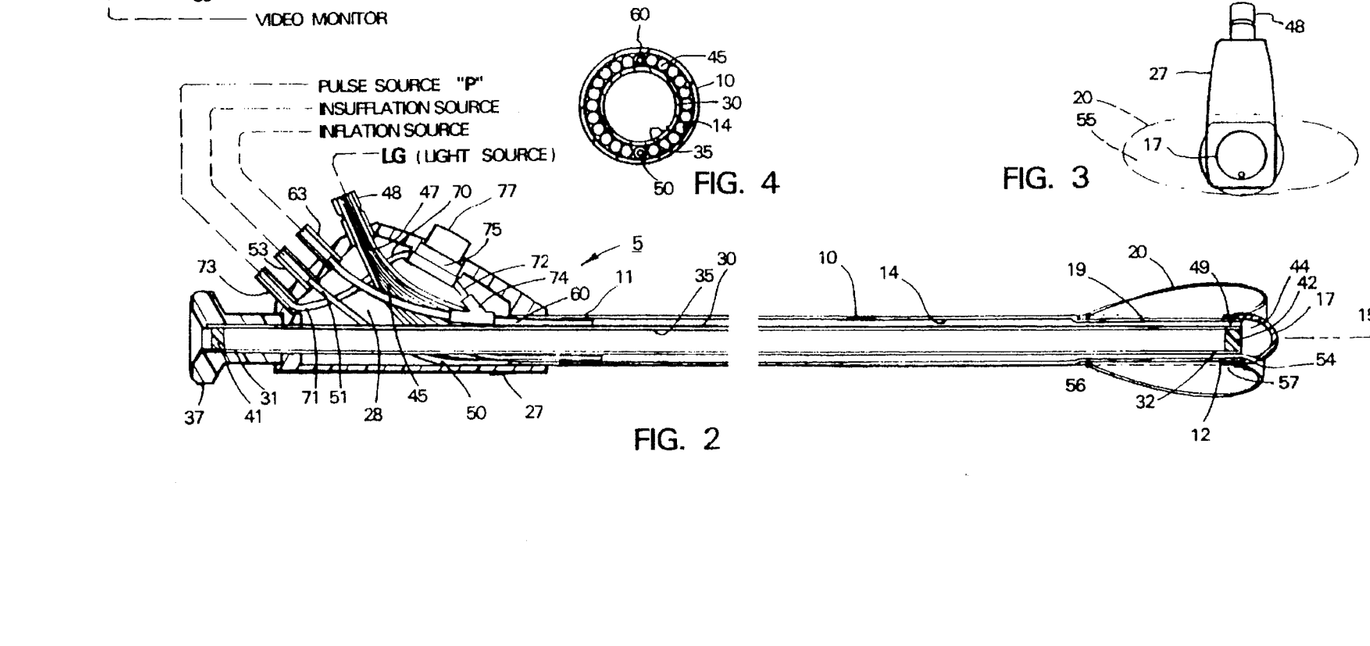
FIG. 2 is a longitudinal partial sectional view of the instrument of FIG. 1 taken along line 2—2 of FIG. 1 rotated 90°.
FIG. 3 is end elevational view of the instrument of FIG. 1 taken along line 3—3 of FIG. 1.
FIG. 4 is a transverse sectional view of the instrument of FIG. 1 taken along line 4—4 of FIG. 1.

FIGS. 1–2 show handle 27 made of plastic mating halves that are joined by any suitable means such as adhesives and form hollow handle interior 28. Proximal end 11 of guide sleeve 10 is fixed in the distal portion of handle 27. FIG. 3 is an end elevational view of handle 27 illustrating its three flat sides that extend minimally radially outward beyond the diameter of guide sleeve 10.

Referring to FIGS. 3–4, optic sleeve 30 with proximal and distal ends, respectively 31 and 32, is made of thin-wall metal or plastic and extends through instrument 5. Sleeve 30 has central bore 35. Proximal end 31 of optic sleeve 30 is fixed in plastic molded eyepiece 37 in the proximal portion of handle 27. Eyepiece 37 is dimensioned to fit to a standard endoscopic video camera 39 shown in phantom view in FIG. 1 to allow the surgeon to operate dissector 5 while viewing a video monitor. Proximal and distal lens elements, respectively 41 and 42, are disposed in the respective proximal and distal ends of bore 35 to provide a suitable field of vision through the bore. Other lens elements (not shown) may be required to provide a suitable field of vision and depth of field. Space 44 is provided between distal lens element 42 and the interior of transparent blunt tip 17 of guide sleeve 10.

FIG. 4 illustrates a transverse sectional view of the instrument with approximately twenty-four (not limiting) optic fibers 45 serving as a light guide (LG). Optic fibers 45 ranging in diameter from 0.001" to 0.01" are dimensioned to fill the concentric space around optic sleeve 30 and within bore 14 of guide sleeve 10. The proximal ends 47 (collectively) of optic fibers 45 are bundled and fixed in male coupling 48 in handle 27. A female push-connector (not shown) coupled to a conventional LG light source may be connected coupling 48. The distal ends 49 of optic fibers 47 are suitably finished for the transmission of light and are fixed in place with adhesives around distal end 32 of optic sleeve 30.

An insufflation mechanism delivers a gas or liquid through guide sleeve 10 and includes longitudinally-extending insufflation tube 50 that has a diameter similar to an optic fiber 45 (see FIG. 2). The proximal end 51 of tube 50 is fixed in Luer-type fitting 53 in handle 27. As can be seen in FIGS. 1–3, tube 50 has open distal termination 54.

Referring to FIGS. 1–2, inflatable sleeve 20 having inflation chamber 55 is disposed around reduced-diameter portion 19 of guide sleeve 10. Inflatable sleeve 20 is made of an elastomeric tubular material such as latex. The proximal end of sleeve 20 is sealably fixed to sleeve 10 by adhesives and annular plastic or metal ring 56. The distal end of sleeve 20 is similarly sealably fixed to sleeve 10 with annular ring 57 thus providing a fluid-tight inflation chamber 55. As can be seen on FIGS. 1–2, blunt tip 17 of guide sleeve 10 is external to inflation chamber 55.

An inflation mechanism inflates sleeve 20 around guide sleeve 10 with an inflation medium, preferably saline solution, $CO_2$ gas or another gas. Referring to FIGS. 2 and 4, inflation tube 60 is disposed in the space between optic sleeve 30 and guide sleeve 10 and is similar in diameter to optic fibers 45. The open distal end of tube 60 communicates with inflation chamber 55 (see FIG. 1). The proximal end of tube 60 is fixed in Luer-type fitting 63 in handle 27. A conventional inflation source (e.g., a syringe) may be provided to supply pressurized liquid or gas to fitting 63 to inflate chamber 55. The inflation medium may be any fluid including a liquid, gas or gel.

Referring to FIG. 2, a pulse mechanism is provided for causing the volume of an inflation medium in inflation chamber 55 to pulse or rapidly increase and decrease in intervals. Pulse tube 70 with proximal and distal ends, respectively 71 and 72, communicates with a pulse source "P", such as a mechanical pump that applies and releases pressure on a liquid or gas inflation medium at intervals. The proximal end 71 of pulse tube 70 is fixed in Luer-type fitting 73 in handle 27. The distal end 72 of pulse tube 70 communicates with inflation tube 60 through branch fitting 74 in handle interior 28. Pulse valve 75 is adapted for actuation by finger pressure and is disposed in the medial portion of pulse tube 70. Pulse trigger 77 is urged to a closed position by a spring (not visible). It can be seen that depressing button 77 opens valve 75 to allow fluid to pass therethrough and communicate with inflation tube 60 and inflation chamber 55. Thus, opening valve 70 will cause the volume of inflation chamber 55 to pulse no matter the volume of inflation medium in the inflation chamber.

The pulse source "P" includes a pressure sensor in its controller 80 that senses when valve 75 is closed thus idling the pulse mechanism. When valve 70 is opened thereby reducing pressure on a fluid reservoir, the pulse mechanism is actuated. The pulse volume, that is the amount by which the volume of inflation chamber 55 increases and decreases, is adjustable by controller 80 and may range from less than 1 per cent to 50 percent or more (not limiting) and depends on the expanded condition of sleeve 20 when pulsed. The pulse interval (time between pulse cycles) of increasing and decreasing the volume of inflation chamber 55 is adjustable at controller 80 and may range e.g. from 100 pulses per second to 1 pulse cycle every 2 seconds (not limiting).

Figure 5:
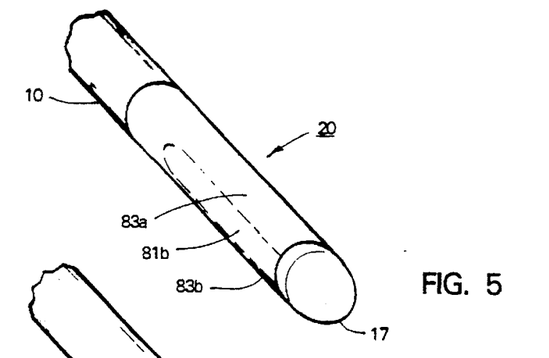
FIG. 5 is an isometric view of the inflation sleeve of FIG. 1.
Figures 6, 7, 8:
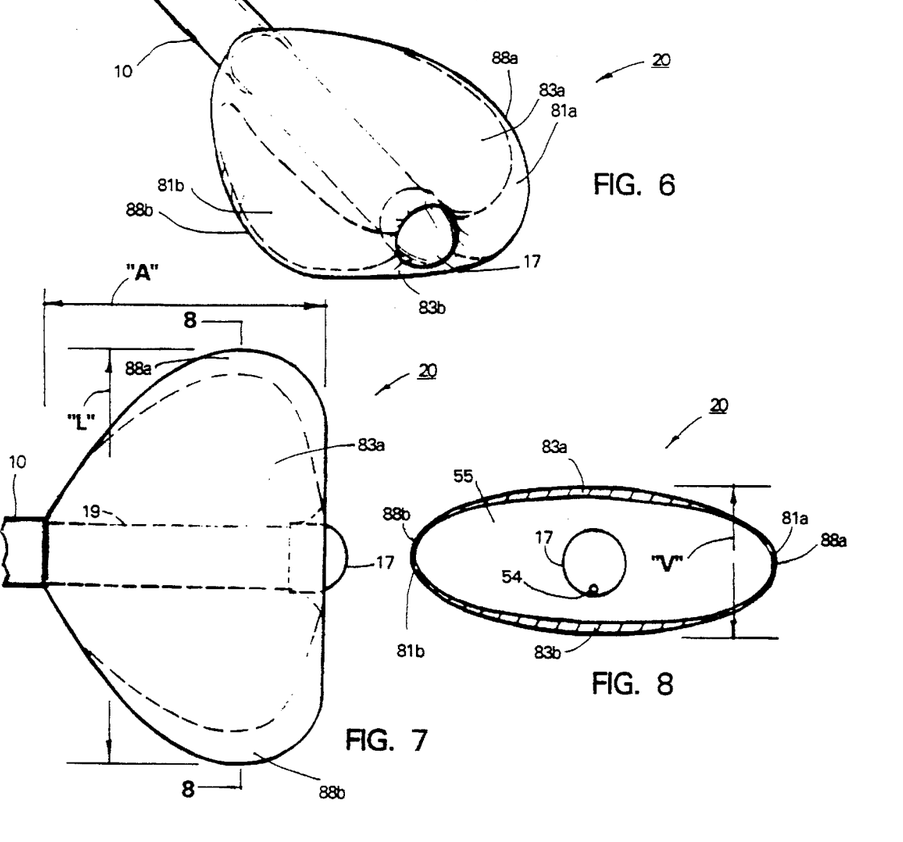
FIG. 6 is an isometric view of the inflation sleeve of FIG. 5 in another position.
FIG. 7 is an elevational view from above of the inflation sleeve of FIG. 6 in another position.
FIG. 8 is a sectional view of the inflation sleeve of FIG. 7 taken along line 8—8 of FIG. 7.

Referring to FIGS. 5–8, inflatable sleeve 20 is "shape-controlled", by which is meant sleeve 20 is preferably made from variably elastic material to induce a particular shape to the sleeve in its expanded position. Such variable elasticity may be by providing variable thickness portions of the wall of sleeve 20. As shown in FIGS. 5–7, thin-wall portions 81a and 81b of inflation sleeve 20 expand more readily under pressure than thick-wall portions 83a and 83b thus providing an inflation sleeve that assumes a flattened shape with laterally-extending side portions 88a and 88b. FIG. 6 shows sleeve 20 in a partially expanded configuration. FIGS. 7–8 show sleeve 20 in a fully expanded configuration. In the transverse sectional view of FIG. 8, sleeve 20 can be seen to have a generally elliptical sectional shape. A variable thickness latex wall for sleeve 20 to induce the flattened sectional shape may be fabricated by progressively dipping portions of sleeve 20 in liquid latex while the sleeve is disposed over a suitable mandril.

Of particular advantage, the expanded plan shape of sleeve 20 is delta-shaped as shown in FIG. 7 and is thus adapted for pulling along a plane in the interior of the body and is adapted to "plow" though connective tissues thereby bluntly stretching and dissecting such tissues. Referring to FIGS. 7–8, the preferred dimensions of sleeve 20 for a TRAM flap include axial dimension "A" in the expanded position ranging from 40 mm. to 70 mm. The preferred lateral dimension "L" in FIG. 7 in the sleeves expanded position ranges from 80 mm. to 120 mm. The preferred vertical dimension "V" in FIG. 8 ranges from 25 mm. to 50 mm. (These dimensions like all others given herein are not limiting).

The use of dissector 5 of FIG. 1 in performing a method in accordance with the present invention now may be described briefly in the mobilization of a rectus abdominus muscle in a TRAM flap procedure as shown in FIGS. 9A–9F and corresponding sectional views FIGS. 10A–10E. The various external connections are made to the instrument including video camera 39 fitted to eyepiece 37. A conventional LG (light source) is connected to fitting 48. An insufflation source is connected to Luer-type fitting 53 and an inflation source is connected to Luer-type fitting 63. The pulse source "P" is connected to Luer-type fitting 73.

Figures 9A, 9B, 10A, 10B:
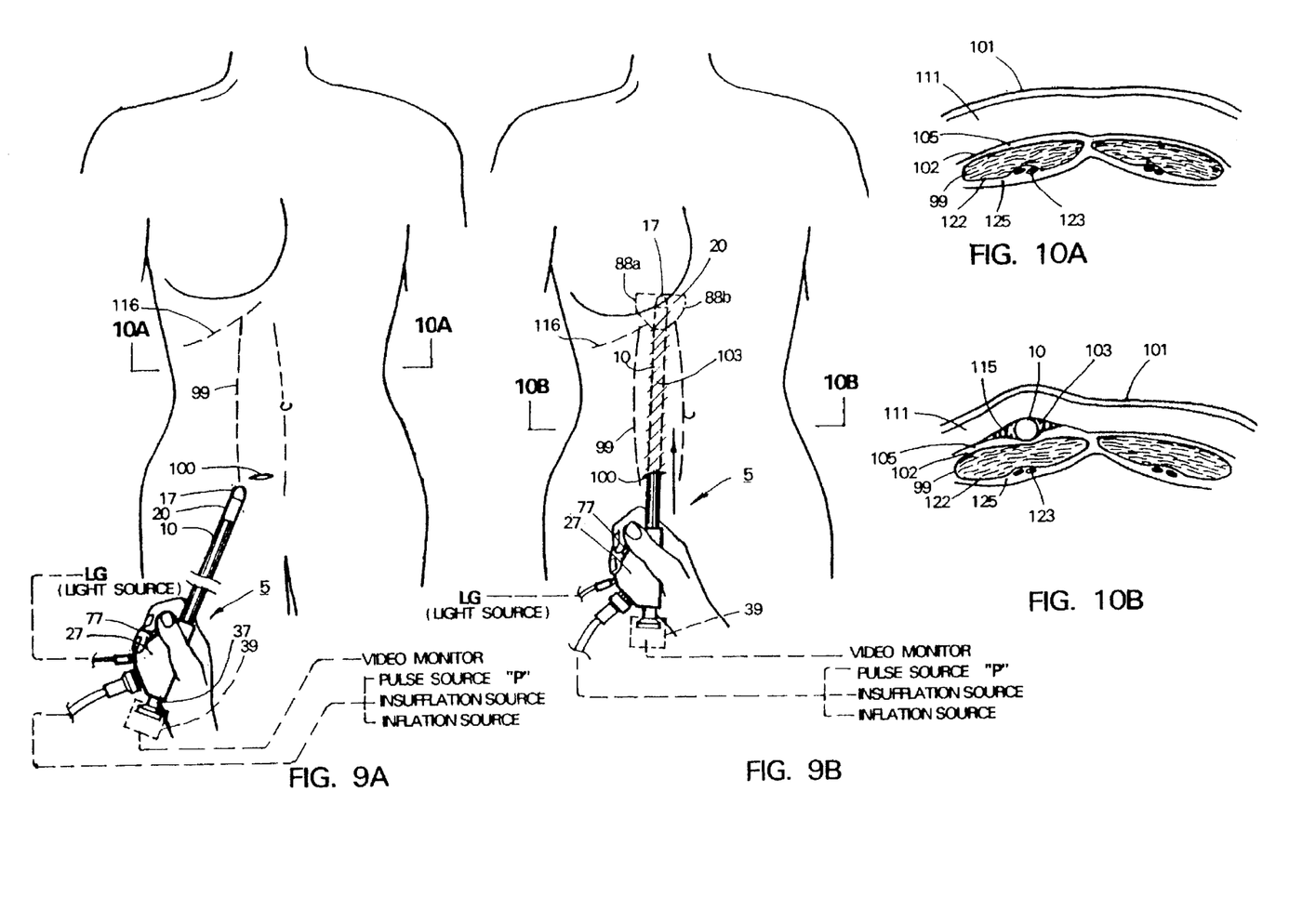
FIGS. 9A–9F show the manner in which the instrument of FIG. 1 is utilized to perform a method in accordance with the present invention.
FIGS. 10A–10E are sectional views of a patients rectus abdominus muscles and surrounding tissues further depicting a method in accordance with the present invention.

Referring to FIG. 9A, assume that the surgical objective is mobilization of rectus abdominus muscle 99 on the patients right side to reconstruct the patients left breast. The patient is prepared with a suitable anesthesia and the surgeon makes a small incision 100 in skin layer 101 in the lower abdomen as shown in FIGS. 9A (see also FIG. 10A). The surgeon inserts the distal tip 17 of guide 10 into incision 100 and then pushes tip 17 inwardly until the tip can be pushed into plane 102 overlying the anterior rectus sheath 105 just above rectus abdominus muscle 99 (see FIG. 10A). It should be appreciated that the dissection also could be made between sheath 105 and muscle 99.

The surgeon then pushes blunt tip 17 upward (distally) along plane 102 toward the costal margin (lower ribs) below the patient's right breast as shown in FIG. 9B thus creating dissected track 103 (see hatched area of FIG. 9B). While thus advancing guide 10, the surgeon views the progress of tip 17 on a video monitor (not shown). As the surgeon applies axial pressure on guide 10, the blunt distalmost tip 17 tends to follow the line of least resistance, i.e., along plane 102 overlying anterior rectus sheath 105 and beneath subcutaneous tissue layers 111 (see FIG. 11A).

As an option, the surgeon may direct an assistant to supply an insufflation medium, such as $CO_2$ gas, under pressure through insufflation tube 50 to insufflate dissected track 103 and plane 102 just in front of tip 17. Such contemporaneous insufflation together with a back and forth movement of tip 17 provides improved vision of dissected track 103 (see hatched area of FIG. 9B) and allows viewing of anatomic structures. Contemporaneous insufflation with saline solution also is possible and will cause certain connective tissues 115 and other tissues to swell and be more visible. Such saline insufflation also may weaken adhesion of connective tissues 115 to allow easier dissection of track 103.

The surgeon pushes tip 17 upwardly (distally) to a second location near costal margin 116 and then stops advancing tip 17. The surgeon may locate costal margin 116 by endoscopic vision, or by the outward "tenting" of skin layer 101 overlying tip 17 and by the emission of light from the LG which causes a spot of light beneath translucent tissue.

With tip 17 and sleeve 20 in a suitable subcostal location as shown in FIG. 9B, the surgeon instructs an assistant to introduce a predetermined amount of inflation medium through inflation tube 60 to expand inflation sleeve 20 to the previously described expanded dimensions at a preferred pressure ranging from 0.025 psi to 2.0 psi (see FIG. 9B). The instrument is rotated angularly so laterally-extending side portions 88a and 88b of sleeve 20 expand laterally outward along plane 102 above the anterior rectus sheath 105.

Figures 9C, 9D, 10C, 10D:
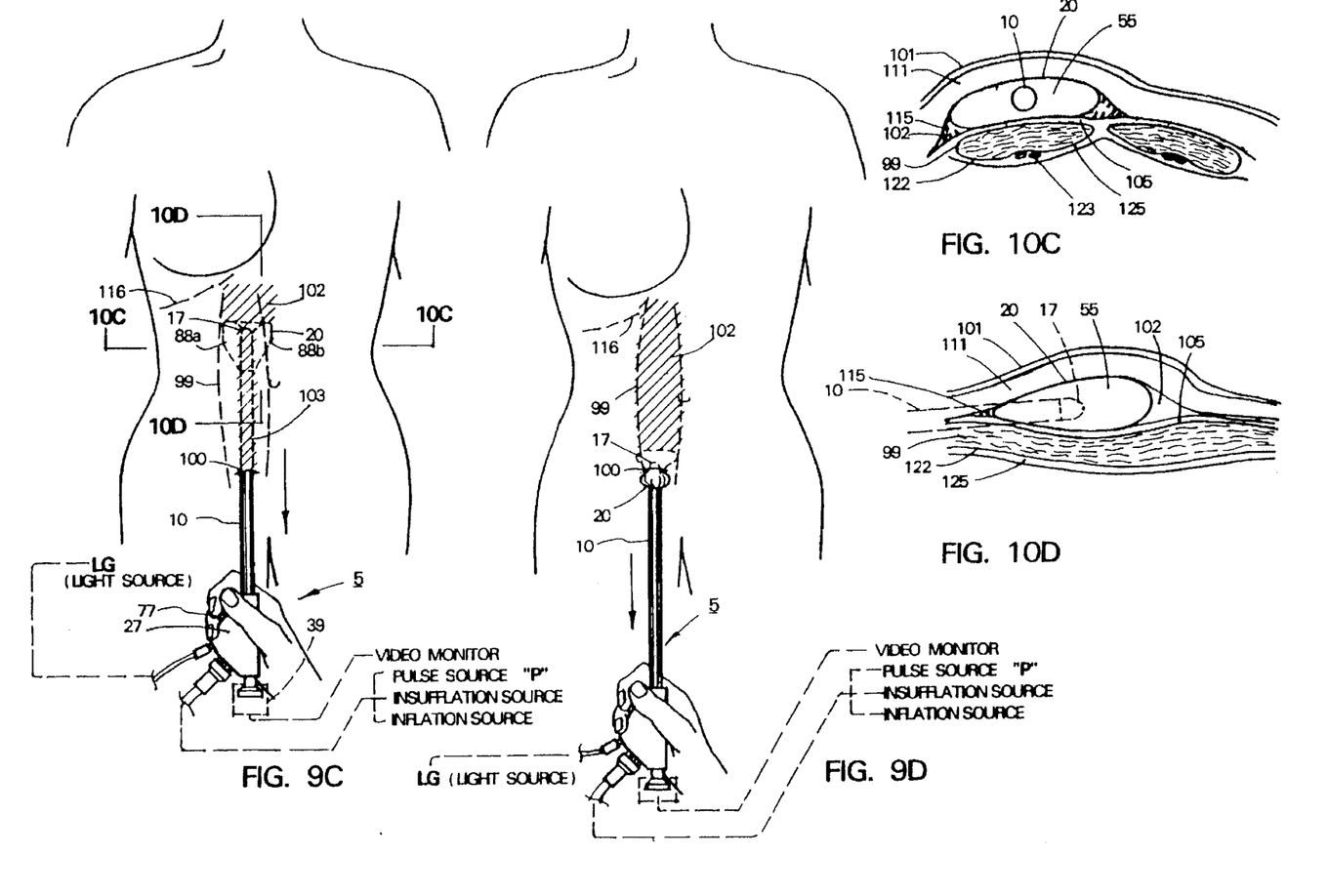

Thereafter, referring to FIG. 9C, the surgeon pulls retrograde dissector 5 and expanded sleeve 20 in reverse along dissected track 103 (proximally). Contemporaneous with the retrograde forces on dissector 5, the surgeon depresses pulse trigger 77 in handle 27 thereby causing inflation sleeve 20 to pulsate. Referring to FIGS. 10C–10D, such pulsations rapidly stretch and relax connective tissues 115 along plane 102 and such stretching followed by tissue rebound constantly readjusts the relation between sleeve 20 and surrounding tissues, thereby dissecting tissues along a plane of least resistance between anterior rectus sheath 105 and overlying particular tissue 111.

Of particular advantage as shown in FIG. 10D, as sleeve 20 is "pulsed" along with the retrograde forces, the sleeve assumes a somewhat "tear-drop" longitudinal sectional shape caused by the resistance of connective tissue along plane 102. Such an induced "tear-drop" shape is optimal for "plowing" connective tissues 115 along plane 102 and pulses in the inflation medium apply forces, in part, perpendicular to plane 102 to dissect connective tissues 115. By comparing FIGS. 9B and 9C, it can be seen that sleeve 20 deforms in its delta-shape as it is pulled proximally. Such elastic characteristics of the wall of sleeve 20 causes minimal damage to blood vessels and thereby creates a relatively blood-free dissected plane 102 (see hatched area of FIG. 9D). The delta-shaped plan of sleeve 20 provides laterally-extending sides 88a and 88b that project outward from the axis of sleeve 10, thereby causing a wide retrograde dissection (approximately 80 mm. to 120 mm.) to mobilize an entire plane 102 overlying rectus abdominus muscle 99. The rate of retrograde movement of sleeve 20 from the subcostal location to incision 100 is rapid (i.e., several seconds depending on pulse intervals).

Of particular advantage as shown in FIG. 9D, the surgeon may pull expanded inflation sleeve 20 outwardly from incision 100 in a single step without deflating the sleeve. As expanded sleeve 20 is pulled through skin layer 101 around incision 100, its shape deforms progressively through multiple hour-glass shapes as the inflation medium moves from the interior to the exterior of skin layer 101. Such progressive deformation of expanded sleeve 20 thus will not measurably stretch or tear resilient skin layer 101.

Figure 9E:
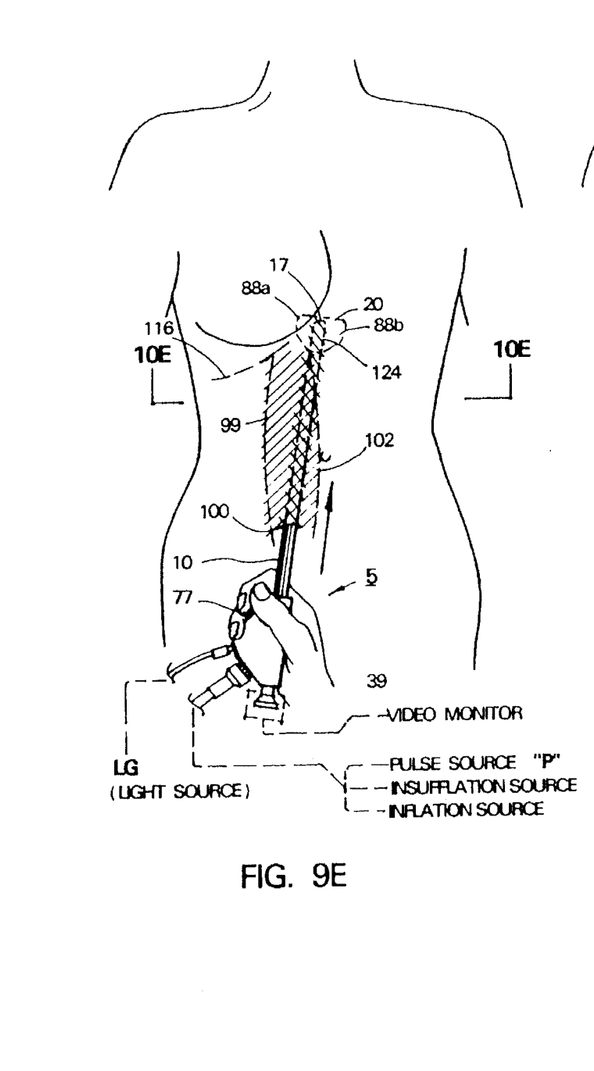
Figure 9F:
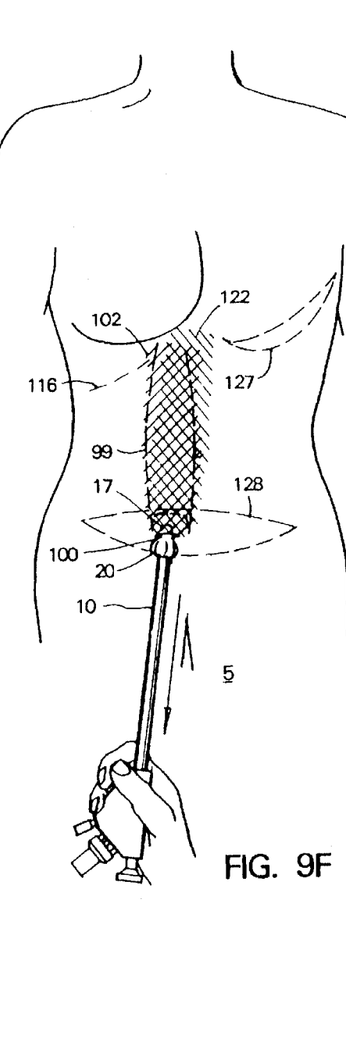
Figure 10E:
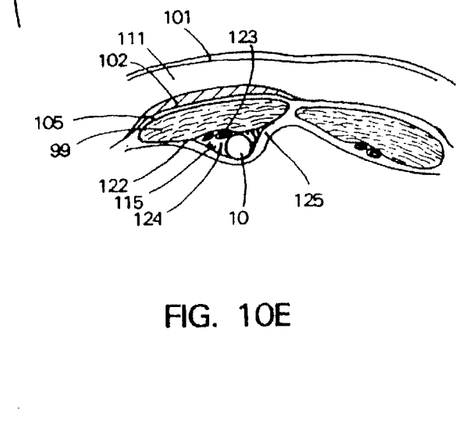

Thereafter, the surgeon identifies plane 122 underlying rectus abdominus muscle 99 just above posterior rectus sheath 125 (see FIG. 10E). Referring to FIG. 9E, the surgeon deflates sleeve 20 and inserts tip 17 into plane 122 and again repeats the method described above of advancing the guide tip 17 upward (distally) to a subcostal location providing dissected track 124. Under endoscopic vision, the surgeon is able to view epigastric artery 123 as tip 17 is pushed distally. As shown in FIGS. 9E–9F, the surgeon then again expands inflatable sleeve 20, pulses the sleeve and pulls expanded sleeve 20 in reverse along track 124 as previously described, this time dissecting connective tissues to provide dissected plane 122 underlying rectus abdominus muscle 99. Thus, in rapid and efficient steps, the surgeon dissects connective tissues and creates dissected planes 102 and 122 (see FIG. 9F) both above and below rectus abdominus muscle 99. The muscle is then mobilized for the remainder of the TRAM flap procedure.

Thereafter, the lower end of rectus abdominus muscle 99 is transsected. The inferior epigastric artery is ligated and transsected and some sharp dissection may be necessary around anterior rectus sheath 105. The above-described blunt dissection leaves the superior epigastric arteriovenous system intact and mobilized within rectus abdominus muscle 99. The remainder of the TRAM flap procedure then may be accomplished in a conventional manner by making left breast incision 127 to receive the imported flap 128. A portion of the anterior rectus sheath 105 and rectus abdominus muscle 99 are then moved to the anterior abdominal wall together with abdominal flap 128 (see FIG. 9F) and thereafter to the breast. In performing the above method, it should be appreciated that the order of utilizing dissector 5 to dissect planes above and below the rectus abdominus muscle may be reversed.

An alternative pulse source "P" utilizes a conventional ultrasonic generator or acoustic transducer that converts electrical energy into mechanical motion. Such a transducer may include a series of piezoelectric elements in a pressurized sandwich between metal elements that cause the metal elements to vibrate or resonate. By exposing the inflation medium to the vibrations caused by the transducer resonating at from 5 kHz to 100 kHz, the inflation medium will transfer mechanical motion to tissue surrounding an expanded inflatable sleeve, thereby facilitating the dissection.

Of particular advantage, a properly "resonating" inflatable sleeve may be capable of transmitting sufficient mechanical motion from the inflation medium to tissue around the expanded sleeve to coagulate dissected blood vessels by denaturing protein in tissues, which in turn will seal such tissues. Also, the resonating sleeve may cause sufficient vibrations in tissue to generate internal tissue friction, thereby developing sufficient heat to cauterize dissected blood vessels and tissue on either side of a dissected plane. Thus, a "resonating" expanded sleeve may assist measurably in creating a relatively blood-free dissected plane. Such a resonating sleeve is useful in other plastic surgeries in which it is necessary to dissect a plane that has a profuse arteriovenous system. Such a resonating sleeve may be maintained in a fixed position for several seconds or moved slowly to cause the desired cauterizing effect on tissue.

A resonating sleeve (not shown) may be provided with inner and outer inflation chambers between concentric inner and outer elastomeric sleeves. An ultrasonic resonating source may communicate only with the outer inflation chamber and the inner chamber will be expanded with a liquid under relatively high pressure of 1 psi to 10 psi to insure that maximum resonating energy is directed outward into surrounding tissue rather being absorbed within the a large volume single inflation chamber.

Figure 11A:
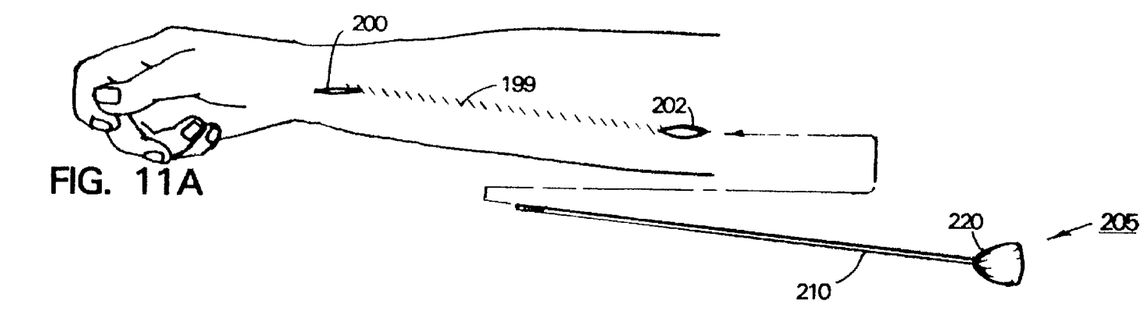
FIGS. 11A–11B show the manner in which an alternative instrument is utilized to perform a method in accordance with the present invention.
Figure 11B:
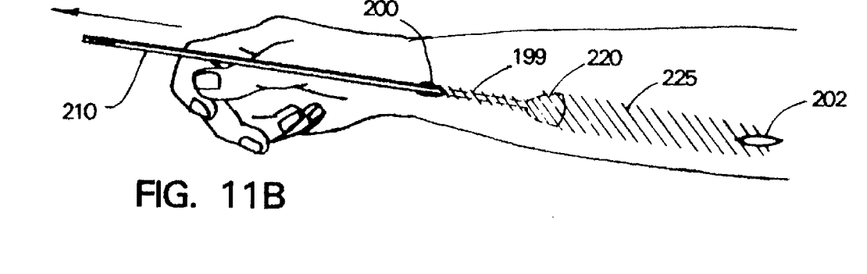

It should be appreciated that the above-described method of pulling a resilient inflated structure in reverse along a dissected track in the interior of the body to "plow" and dissect connective tissues may be accomplished in various ways and be within the scope of the present invention. For example, an arteriovenous graft procedure is shown in FIGS. 11A–11B. In FIG. 11A, a commercially available tunneler such as an "Impra Kelly-Wick Access Tunneler KW2000"

may be used to dissect a track 199 (hatched area) in subcutaneous tissue between a first wrist incision 200 and a second forearm incision 202.

Figure 11C:
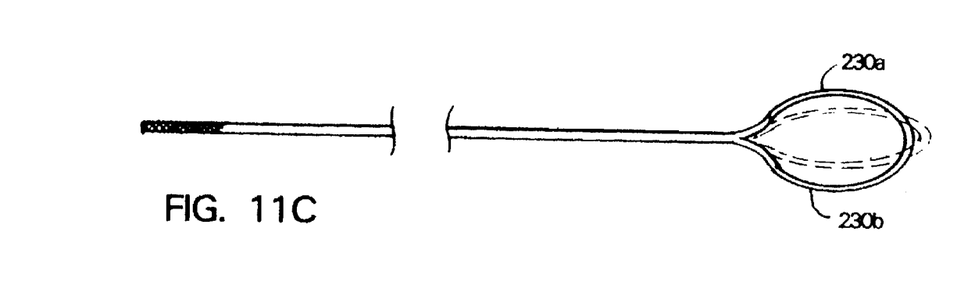
FIG. 11C is an alternative embodiment of a portion of the present invention.

Retrograde dissector 205 with elongate member 210 attached to inflatable structure 220 then may be inserted through dissected track 199 (from either direction). As shown in FIG. 11B, the surgeon then may pull inflatable structure 220 through a skin incision and along track 199 to dissect connective tissues thereby providing a larger diameter dissected plane 225 (hatched area) of FIG. 11B. Thereafter, a vein may be pulled easily into the dissected plane 225 for grafting. Referring to FIG. 11C, it should be appreciated that a flexible plastic bowed-structure may be pulled in reverse along track 199, such as the device of FIG. 11C having laterally-extending flexible plastic bows 230a-230b. The bows 230a-230b may be covered with an elastomeric sleeve or left uncovered.

It should also be appreciated that a retrograde dissector 5 may be "pulsed" with sleeve 20 in the contrasted position as depicted in FIG. 5. Such pulsing may be utilized when the instrument is advanced distally through subcutaneous tissue to facilitate the dissection of the first track through tissue. Such pulsing may be useful when the track is adjacent to a vein or artery to help insure that such structures are not injured by the distal advancement of the instrument.

Figure 12A:
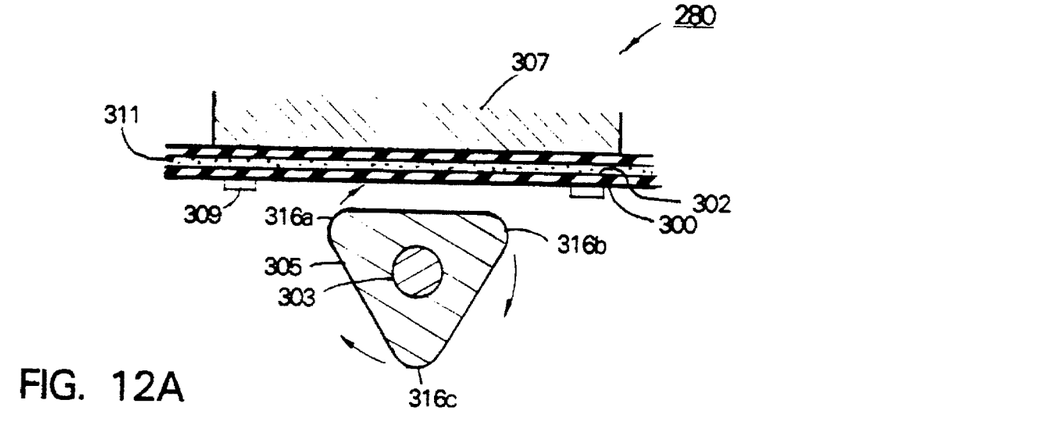
FIGS. 12A–12C are sequential views of a portion of a pump in accordance with the present invention.
Figure 12B:
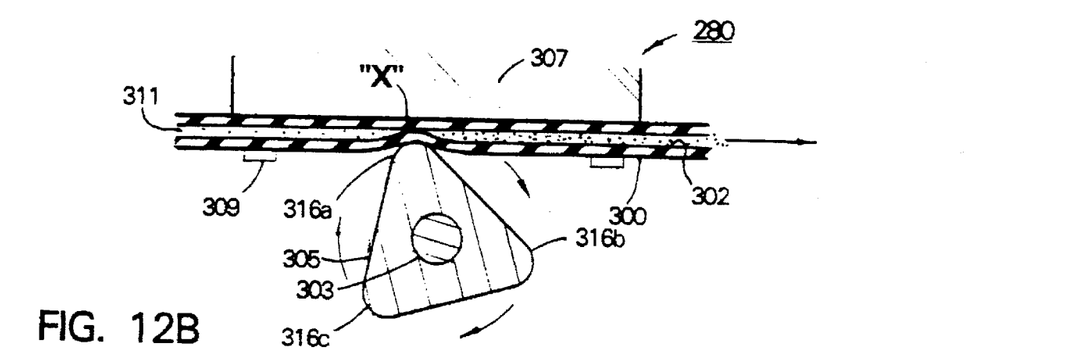
Figure 12C:
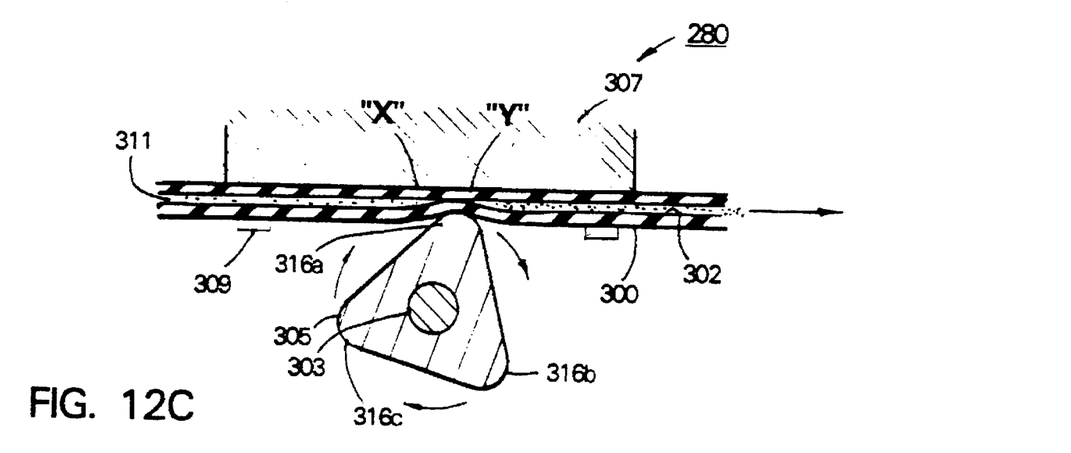

Dissector 5 was described above with either a mechanical pump or an acoustic transducer serving as pulse mechanism "P" As shown in FIGS. 12A-12C, a particular type of pulse controller 280 is suitable for an operating room. Controller 280 advantageously does not need to be sterilized to pump a fluid through distensible tube 300 with bore 302 and the controller may pump fluid at a wide range of pulse intervals and pulse volumes. Such pulse intervals may range for example, from 1000 pulses per second to 1 pulse per second or less by changing the speed of revolution of motor driven shaft 303 turning rotor 305 (see FIG. 12A). The volume of pulses may vary by using different diameters for bore 302.

Controller 280 is adapted to secure resilient tube 300 having bore 302 against wall portion 307 of the device. Spring clips 309 hold pulse tube 300 in position. Pulse tube 300 is made of any suitable distensible material such as vinyl or latex. The diameter of tube 300 may range from 0.100" to 0.400" (not limiting). Bore 302 may range in diameter from 0.010" to 0.250" with the volume within a portion of bore 302 determining the pulse volume as described below.

It can be seen in the sequence of movements of rotor 305 in FIGS. 12A-12C, that fluid medium 315 may be pulsed in pulse tube 300. In FIG. 12A, rotor 305 is rotating in clockwise movement and rotor arm tips 316a, 316b and 316c are disposed such that resilient tube 300 is in a repose position. In FIG. 12B, rotor arm tip 316a has rotated approximately 15° such that tip 316a has compressed resilient tube 300 thereby closing bore 302 at point "X". In FIG. 12C, rotor arm tip 316a has rotated further approximately 15° thus progressively moving the point of closure of bore 302 from point "X" to point "Y". The "rolling" closure of bore 302 between points "X" and "Y" thereby pumps fluid medium 311 in the distal direction. Thereafter, further rotation of rotor 315 causes the rotor arm tips to return to the relative positions of FIG. 12A allowing tube 300 to return to it repose position thereby opening bore 302 and allowing fluid medium 311 to reverse flow, for example under the pressure exerted by a distal elastomeric sleeve as it resists inflation. Thus, it can be seen that rotation of rotor 315 sequentially will apply and release distal pumping pressure on fluid medium 311 to provide distal pulsing of the inflation medium.

The speed of rotation of shaft 303 may be variable, e.g., from 20 rpm to 2000 rpm (not limiting), to provide a wide range of pulse intervals, respectively from one pulse/second to 1000 pulses/second. The rotating shaft 303 may be rotated by an electric or air motor or any other suitable means. It should be appreciated that rotor arm tips 316a, 316b and 316c may be positioned to not entirely close bore 302 between points "X" and "Y". Such positioning of the rotor arm tips relative to sleeve 300 will cause distal "surges" of inflation medium 311 as the rotor 305 rotates and bore 302 moves between "restricted" and "less restricted" bore dimensions.

Figure 13:
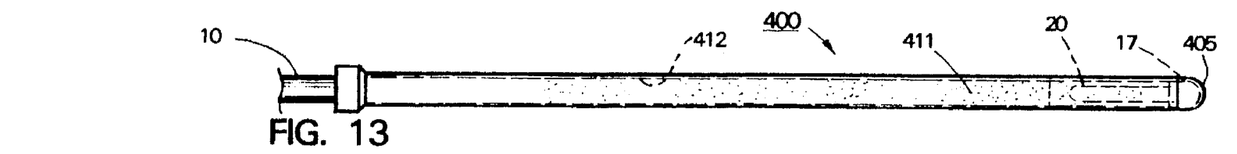
FIG. 13 is a plan view of a tubular sheath in accordance with the present invention.
Figure 14:
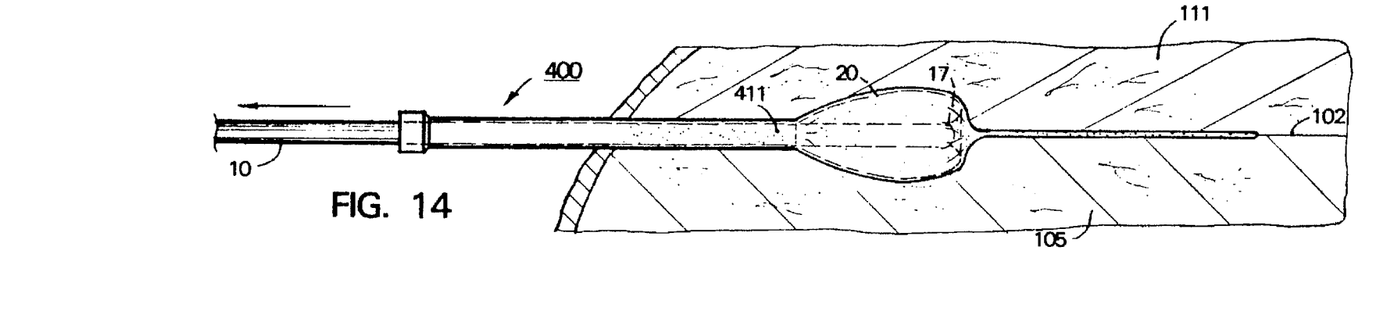
FIG. 14 is a partial sectional view of the sheath of FIG. 13 in use.

The above-described dissector also may be utilized with friction-reducing sheath 400 as shown in FIGS. 13-14. Sheath 400 is made of latex or other suitable elastomeric material having a wall thickness ranging from 0.005" to 0.010" (not limiting). The distal end 402 of sheath 400 has a clear plastic film tip 405 that fits closely around blunt tip 17 of dissector 5. The distal portion of sheath 400 is textured on its exterior having, for example, a rough sand-blast type finish 411. Sheath 400 is adapted to encase elongate guide sleeve 10 and inflatable sleeve 20 of dissector 5 and the inflatable sleeve will expand within the sheath as shown in FIG. 14.

In operation of dissector 5 and sheath 400, referring to FIG. 14, the dissector is used as previously described to dissect plane 102 overlying anterior rectus sheath 105 and under subcutaneous tissue layer 111. As sleeve 20 is inflated, the sand-blast type finish 411 of the exterior of sheath 400 frictionally engages tissue layers surrounding the sheath. As the surgeon pulls delta-shaped expanded sleeve 20 proximally as shown in FIG. 14, the sheath 400 frictionally "sticks" or remains in place in dissected plane 102 between anterior rectus sheath 105 and overlying subcutaneous tissue layer 111. The retrograde movement of sleeve 20 within sheath 400 prevents friction between expanded sleeve 20 and surrounding tissue. The interior surface of the lumen 412 in sheath 400 is smooth and is adapted to cause little friction with the surface of sleeve 20 to allow its retrograde movement within the sheath. After the expanded sleeve is removed from the incision, sheath 400 then also may be pulled out of the incision. The above-described method will cause a "retrograde" dissection of a plane between muscles with greater radial dissecting forces and lesser axial (frictional) forces on the tissue layers.

Figure 15:
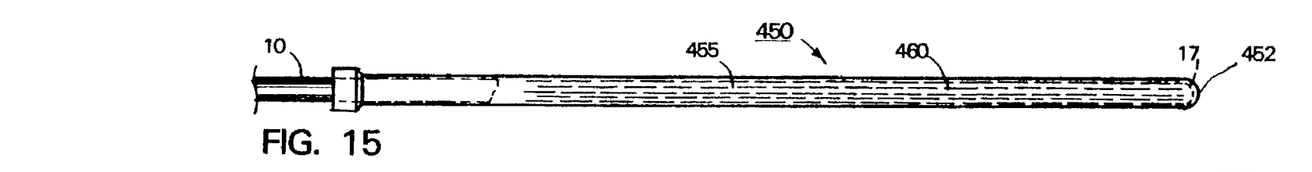
FIG. 15 is a plan view of an alternative embodiment of a tubular sheath.
Figure 16:
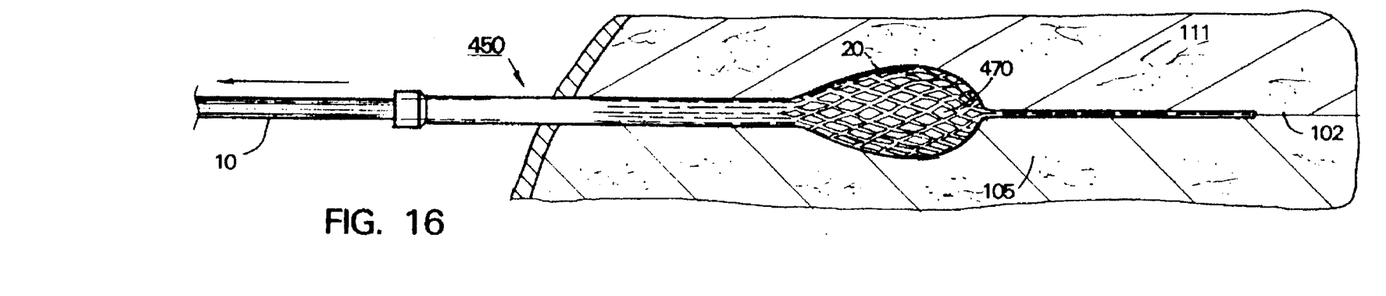
FIG. 16 is a partial sectional view of the sheath of FIG. 15 in use.

The above-described dissector 5 also may be utilized with friction-reducing sheath 450 as shown in FIGS. 15-16. Sheath 450 is made of non-elastomeric material, such as polyurethane sheet or PEI® material, having a wall thickness ranging from 0.001" to 0.005" (not limiting). The distal end 452 of sheath 450 is formed to fit closely around blunt tip 17 of dissector 5. The wall 455 of sheath 450 has "weakened-plane" lines 460 (collectively) impressed into its surface. Sheath 450 is adapted to encase guide sleeve 10 and inflatable sleeve 20 of dissector 5 in its contracted state. As inflatable sleeve 20 is inflated to its expanded state, the inflation pressure causes "weakened-plane" lines 460 to split into perforations 470 (see FIG. 16) thus allowing the non-elastomeric sheath 450 to accommodate the expanded sleeve 20.

The operation of dissector 5 and sheath 450, referring to FIG. 16, is similar to the method described above utilizing sheath 400. As sleeve 20 is inflated within sheath 450, the perforated surface of sleeve 450 frictionally engages tissue layers, 111 and 105, surrounding the sheath. As the surgeon pulls delta-shaped expanded sleeve 20 proximally as shown in FIG. 16, sheath 450 remains in place in dissected plane 102 between anterior rectus sheath 105 and overlying subcutaneous tissue layer 111. Thus, the retrograde movement of sleeve 20 within sheath 400 prevents friction between expanded sleeve 20 and surrounding tissue.

It should be appreciated that sheaths 400 and 450 allow the use of a non-elastomeric inflatable sleeve that will be constrained in its contracted position by the sheath for insertion into a plane between tissues. An inflatable sleeve made of non-elastomeric material allows for a special shape expanded sleeve (e.g. a flatter sleeve) that may not be possible using variably elastic material.

The above-described dissector 5 includes built-in endoscopic viewing lens elements and fiber optic LG. It should be appreciated that an instrument with an inflatable structure and "pulse" source may be adapted with a longitudinally-extending lumen to receive a conventional endoscope. The dissector also may provided with a non-elastomeric inflatable sleeve carried in a conraining sleeve similar to the disclosure of U.S. Pat. No. 5,569,183.

Although the present method is for dissecting planes underlying and overlying a muscle in a TRAM flap procedure, it should be appreciated that the device and method can be used for other surgical procedures. For example, the instrument and method can be used for any procedure in which it is useful to dissect planes around muscles.

This disclosure is illustrative and not limiting. Further variations will be apparent to one skilled in the art in light of this disclosure and are intended to fall within the scope of the appended claims.

What is claimed is:

1. A method dissecting connective tissues, comprising the steps of:

introducing a distal blunt tip of an elongate guide into a tissue plane in the interior of a body in a first location;

advancing said blunt tip distally along said tissue plane to a second remote location; and together with the advancing step, pulsing an inflatable structure at said blunt tip, thereby bluntly dissecting connective tissues along said tissue plane.

2. The method of claim 1, wherein the introducing step is preceded by a step of making an incision through overlying tissue to access said tissue plane.

3. The method claim 1, wherein the advancing step includes the step of viewing through said guide said tissue plane being dissected around said blunt tip.

4. The method claim 1, wherein the advancing step includes he step of insufflating the dissected tissue plane with a fluid flowing through said blunt tip.

5. A method for dissecting connective tissues comprising the steps of:

introducing a distal tip of an elongate guide into a tissue plane in the interior of a body in a first location;

advancing said tip distally along said tissue plane to a second remote location thereby dissecting a track;

expanding an inflatable structure disposed at said distal tip; and pulling said inflatable structure in an expanded state along said track from the second location to the first location thereby dissecting connective tissues along said tissue plane.

6. The method of claim 5, wherein the pulling step includes the step of pulsing an inflation medium within said inflatable structure.

7. The method of claim 5, wherein said inflatable structure has an elliptical transverse sectional shape and the step of pulling includes dissecting connective tissues substantially laterally outward from said axis along said tissue plane.

8. The method of claim 5, further comprising the step of proximally pulling said inflatable structure in an expanded state from the interior of the body to the exterior of the body through an incision in an overlying skin layer, thereby elastically deforming said inflatable structure so as to not tear said skin layer.

9. The method of claim 5, further comprising the step of ultrasonically exciting an inflation medium in said inflatable structure, thereby transferring ultrasonic energy to tissue surrounding said inflatable structure and thereby cautering dissected blood vessels.

10. A surgical method for dissecting connective tissues comprising the steps of:

creating a small diameter dissected subcutaneous track in an interior of a body between a first location and a second location;

locating an inflatable structure at one of said first and second locations; and pulling said inflatable structure in an expanded state having a transverse sectional dimension larger than said dissected track along said track towards the other of said first and second locations, thereby dissecting connective tissues and enlarging said dissected track.

11. A method for dissecting connective tissues in a body, comprising the steps of:

introducing a distal tip of an elongate guide into a plane between tissues in the interior of the body in a first location;

expanding an inflatable structure disposed at said distal tip, thereby bluntly dissecting connective tissues along said plane; and pulling said inflatable structure in an expanded state from said first location to a second location nearer an exterior of the body.

12. A method for dissecting connective tissues in a body comprising the steps of:

introducing a distal tip of an elongate guide within a tubular sheath into a tissue plane in an interior of the body in a first location;

advancing said tip distally along said tissue plane to a second remote location thereby dissecting a track;

expanding an inflatable structure disposed at said distal tip; and pulling said inflatable structure in an expanded state within said tubular sheath and along said track from the second location to the first location, thereby dissecting connective tissues along said tissue plane and leaving said tubular sheath within said track.

13. The method of claim 12, further comprising the step of pulling said tubular sheath out of said dissected track.

* * * * *